US00PP27310P2

(12) United States Plant Patent
Klemm et al.

(10) Patent No.: US PP27,310 P2
(45) Date of Patent: Oct. 25, 2016

(54) *PETUNIA* PLANT NAMED 'KLEPH15254'

(50) Latin Name: *Petunia hybrida*
Varietal Denomination: KLEPH15254

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 14/545,760

(22) Filed: Jun. 15, 2015

(51) Int. Cl.
*A01H 5/02* (2006.01)

(52) U.S. Cl.
USPC ..... Plt./356.18

(58) Field of Classification Search
USPC ..... Plt./356.18
CPC ..... A01H 5/02
See application file for complete search history.

*Primary Examiner* — Kent L Bell
(74) *Attorney, Agent, or Firm* — Bethany R. Roahrig; Barbara Campbell; Cochran Freund & Young, LLC

(57) ABSTRACT

A new *petunia* plant particularly distinguished by having magenta purple colored flowers and an upright and mounding plant habit, is disclosed.

1 Drawing Sheet

Genus and species: *Petunia hybrida.*
Variety denomination: 'KLEPH15254'.

BACKGROUND OF THE NEW PLANT

The present invention comprises a new and distinct variety of *petunia*, botanically known as *Petunia hybrida*, and hereinafter referred to by the variety name 'KLEPH15254'. 'KLEPH15254' originated from a controlled-cross between the proprietary female *petunia* variety 'PH-2008-0333' (unpatented) and male proprietary *petunia* variety 'PH-2010-1781' (unpatented).

In July 2011, two *petunia* parental lines, the female *petunia* variety 'PH-2008-0333' and the male *petunia* variety 'PH-2010-1781' were crossed via a controlled cross in Latina, Italy and seeds were obtained. The seeds were sown and plants were grown for evaluation. A plant line was selected in April 2012 which had magenta purple colored flowers and was subsequently named 'KLEPH15254'. In May 2012, 'KLEPH15254' was first vegetatively propagated by terminal tip cuttings and tissue culture in Latina, Italy. 'KLEPH15254' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Magenta purple colored flowers; and
2. An upright and mounding plant habit.

DESCRIPTION OF THE PHOTOGRAPH

This new *petunia* plant is illustrated by the accompanying photograph which shows the flowers and foliage of the plant grown in a pot. The photograph is of a three-month-old plant grown in the greenhouse in Stuttgart, Germany in May 2014.

The colors shown are as true as can be reasonably obtained by conventional photographic procedures.

DESCRIPTION OF THE NEW VARIETY

The following detailed descriptions set forth the distinctive characteristics of 'KLEPH15254'. The data which define these characteristics were collected from asexual reproductions carried out in Latina, Italy. Data was collected on twelve-week-old plants grown in plastic greenhouse in Latina, Italy in February 2015. Color references are to The R.H.S. Colour Chart of The Royal Horticultural Society of London (R.H.S.), $5^{th}$ edition (2007).

Classification:
- *Family.*—Solanaceae.
- *Species.*—*Petunia hybrida.*
- *Common name.*—*Petunia.*
- *Variety.*—'KLEPH15254'.

Parentage:
- *Female.*—Proprietary female *petunia* 'PH-2008-0333' (unpatented).
- *Male.*—Proprietary male *petunia* 'PH-2010-1781' (unpatented).

Plant description:
- *Form.*—Compact growth.
- *Habit.*—Upright and mounding.
- *Height (from top of soil).*—About 9.0 cm.
- *Width.*—About 13.0 cm.
- *Propagation.*—Terminal tip cuttings and tissue culture.
- *Time to produce a finished flowering plant.*—About 13 weeks in winter under short day conditions; 7 weeks in spring.
- *Time to initiate and develop roots.*—2 to 3 weeks.
- *Root description.*—Moderate density, moderate branching, white roots.

Stems:
- *Average number (basal).*—15.
- *Length of basal branches (from the base of the stem to the tip).*—6.5 cm.

*Internode length.*—0.6 cm.
*Diameter of branches* (*from midpoint*).—0.3 cm.
*Stem color.*—RHS 145C.
*Anthocyanin.*—Absent.
*Texture.*—Tomentose.

Leaves:
*Arrangement.*—Alternate.
*Length.*—5.0 cm.
*Width.*—2.5 cm.
*Shape.*—Elliptic.
*Apex.*—Acute.
*Base.*—Attenuate.
*Margin.*—Entire.
*Immature leaf color.*—Upper surface: RHS 137B. Lower surface: RHS 146D.
*Mature leaf color.*—Upper surface: RHS N137C. Lower surface: RHS 138A.
*Texture* (*both surfaces*).—Tomentose.
*Venation pattern.*—Arcuate.
*Venation color* (*both surfaces*).—RHS 146B.
*Petioles.*—Length: 1.0 cm. Diameter: 0.3 cm. Color: RHS 145C. Texture: Tomentose.

Flower buds:
*Shape.*—Irregular to oblong.
*Length.*—3.5 cm.
*Diameter.*—0.5 cm to 0.8 cm.
*Color at tight bud.*—RHS 83B.
*Texture.*—Slightly pubescent.

Inflorescence:
*Blooming habit* (*flowering season*).—Permanent flowering during the summertime.
*Inflorescence type.*—Cymose.
*Number of flowers per node.*—1.
*Lastingness of individual blooms on the plant.*—About 1 week.
*Fragrance.*—Absent.
*Flowers.*—Arrangement: Composed of 5 petals fused at the base. Diameter (flower face): 5.5 cm. Depth (total length of flower): 5.0 cm. Throat/Funnel: Length: 2.5 cm. Diameter (at opening): 1.2 cm. Texture (both inner and outer surfaces): Smooth, glabrous. Color: Inner surface: RHS 86A. Outer surface: RHS 142C and RHS 85A. Petals: Color, mature flower (fully opened): Upper surface: Closest to RHS N78A. Lower surface: RHS N78C. Apex: Mucronate. Base: Fused. Shape: Base fused in a funnel. Margin: Entire. Strength of waviness: Weak. Degree of lobation: Weak. Calyx arrangement: Actinomorphic, composed of 5 sepals.
*Sepals.*—Color: Upper surface: RHS N137B. Lower surface: RHS 137C. Length: 2.0 cm. Width: 0.5 cm. Shape: Narrowly oblong. Apex: Acute. Base: Attenuate. Margin: Entire. Texture (both surfaces): Slightly pubescent.
*Pedicels.*—Color: RHS 144B. Length: 4.0 cm. Diameter: 0.1 cm. Texture: Pubescent.

Reproductive organs:
*Stamens.*—Quantity: 5. Shape: Needle like with elliptic head. Filament: Length: 1.3 cm to 2.0 cm. Diameter: 0.08 cm. Color: RHS 145C. Anther: Shape: Ovate. Color: RHS 145D. Length: 0.15 cm. Diameter: 0.12 cm. Pollen: Color: RHS 190B. Amount: Abundant.
*Pistils.*—Quantity per flower: 1. Length: 2.0 cm. Stigma color: RHS 144A. Style color: RHS 145B and RHS N77C.

Fruit/seed set: None observed.
Disease/insect resistance: None observed.

COMPARISON WITH PARENTAL LINES AND KNOWN VARIETY

'KLEPH15254' is a distinct variety of *petunia* and is distinguished from its parents as described in Table 1:

TABLE 1

Comparison with Parental Lines

| Trait | Variety 'KLEPH15254' | Female parent 'PH-2008-0333' | Male Parent 'PH-2010-1781' |
|---|---|---|---|
| Plant habit | More compact than 'PH-2008-0333' | More vigorous than 'KLEPH15254' | |
| Flower size | Smaller flower than both parents | Bigger flower than 'KLEPH15254' | Bigger flower than 'KLEPH15254' |

'KLEPH15254' is most similar to the commercial line *petunia* plant named Sanguna Patio Purple (patent status unknown). Differences between the two varieties are described in Table 2:

TABLE 2

Comparison with Similar Variety

| Trait | Variety 'KLEPH15254' | Commercial line Sanguna Patio Purple |
|---|---|---|
| Flower color | Magenta purple | Dark purple |

We claim:

1. A new and distinct variety of *petunia* plant named 'KLEPH15254' as illustrated and described herein.

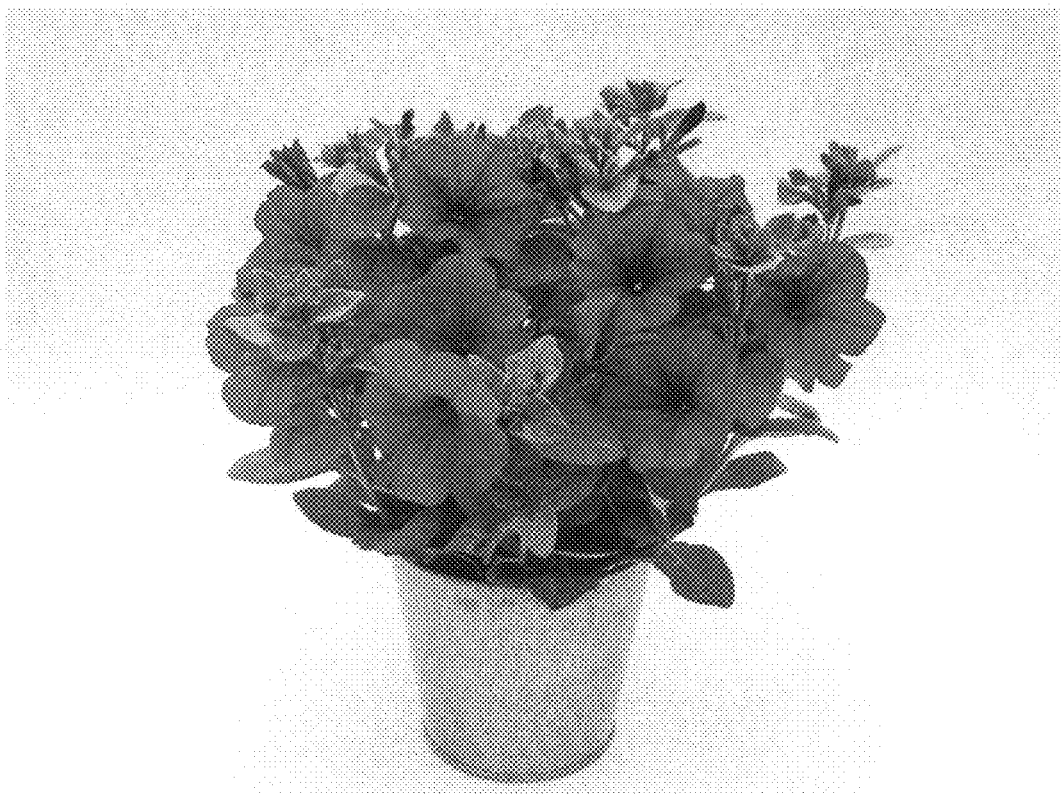

* * * * *